(12) United States Patent
Cohen

(10) Patent No.: US 8,052,599 B2
(45) Date of Patent: Nov. 8, 2011

(54) ENDORECTAL TROCAR

(75) Inventor: Jean-Pierre Cohen, Mougins (FR)

(73) Assignees: Jean-Pierre Cohen, Mougins (FR); Aspide Medical, La Talaudiere (FR)

( * ) Notice: Subject to any disclaimer, the term of this patent is extended or adjusted under 35 U.S.C. 154(b) by 470 days.

(21) Appl. No.: 12/262,559

(22) Filed: Oct. 31, 2008

(65) Prior Publication Data

US 2009/0124862 A1     May 14, 2009

(30) Foreign Application Priority Data

Oct. 31, 2007    (FR) ...................................... 07 58738

(51) Int. Cl.
*A61B 1/32* (2006.01)
(52) U.S. Cl. .......................... 600/235; 600/213; 600/226
(58) Field of Classification Search .................. 600/201, 600/205, 208, 213, 226, 235
See application file for complete search history.

(56) References Cited

U.S. PATENT DOCUMENTS

| 4,538,594 | A |   | 9/1985  | Boebel et al. |
|-----------|---|---|---------|---------------|
| 5,256,149 | A | * | 10/1993 | Banik et al. ............... 604/164.01 |
| 5,569,205 | A | * | 10/1996 | Hart et al. ................ 604/167.03 |
| 6,162,196 | A |   | 12/2000 | Hart et al. |

FOREIGN PATENT DOCUMENTS

FR      2 536 651       6/1984

OTHER PUBLICATIONS

French Search Report corresponding to FR Application No. 07/58738 filed Oct. 31, 2007.

* cited by examiner

*Primary Examiner* — Eduardo C Robert
*Assistant Examiner* — Ellen C Hammond
(74) *Attorney, Agent, or Firm* — Young & Thompson

(57) ABSTRACT

An endorectal trocar provided with body for endorectal introduction that defines open internal channel and leak-tight barrier that extends across internal channel and exhibits passageways for rectoscopy instruments, the body and the leak-tight barrier are two distinct assemblies that can be attached by the fixing elements within the internal channel.

16 Claims, 6 Drawing Sheets

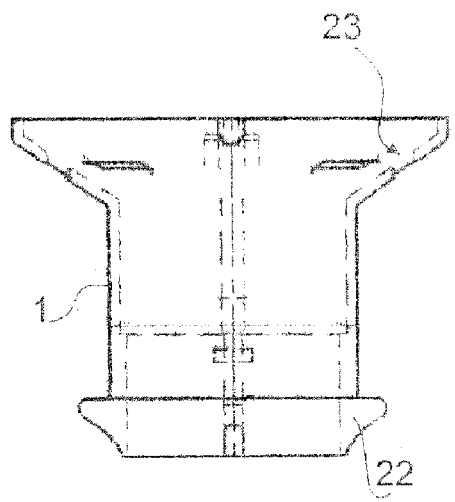
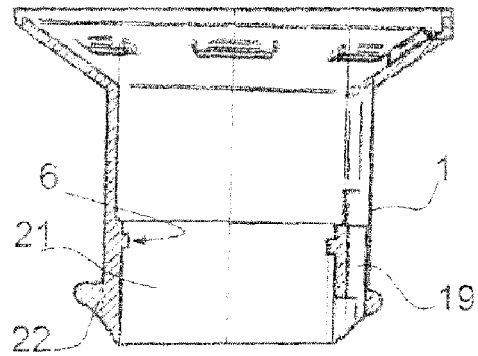
Fig.1    Fig.2
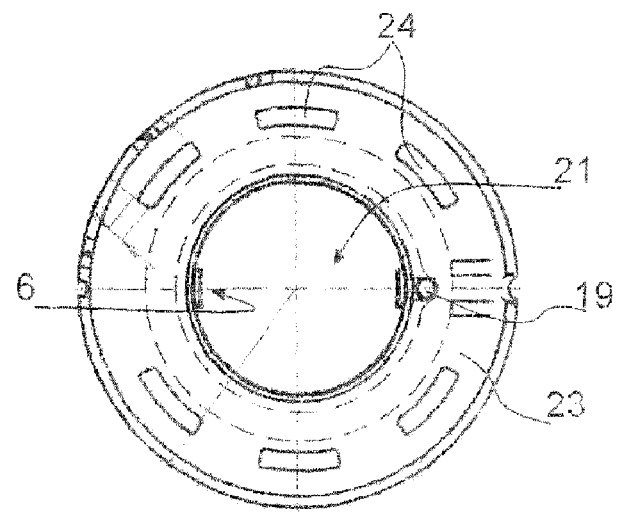
Fig.3

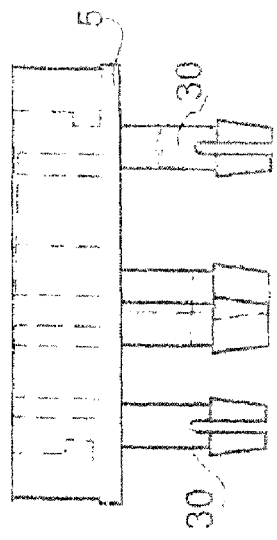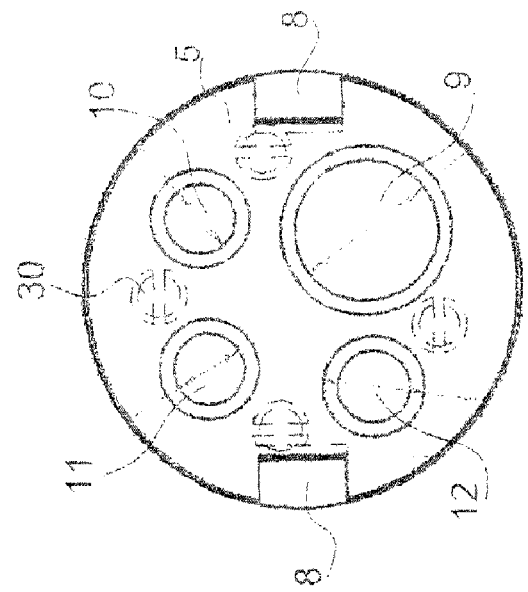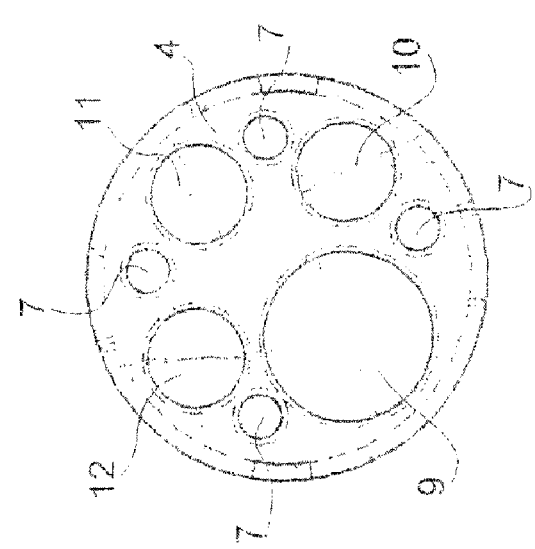

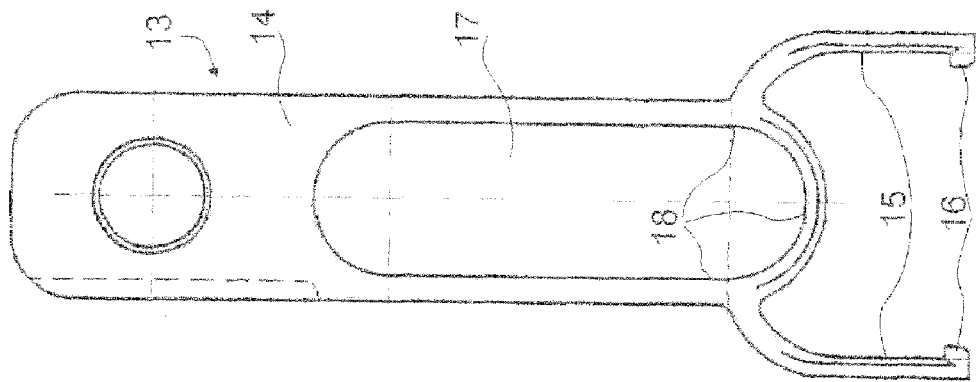
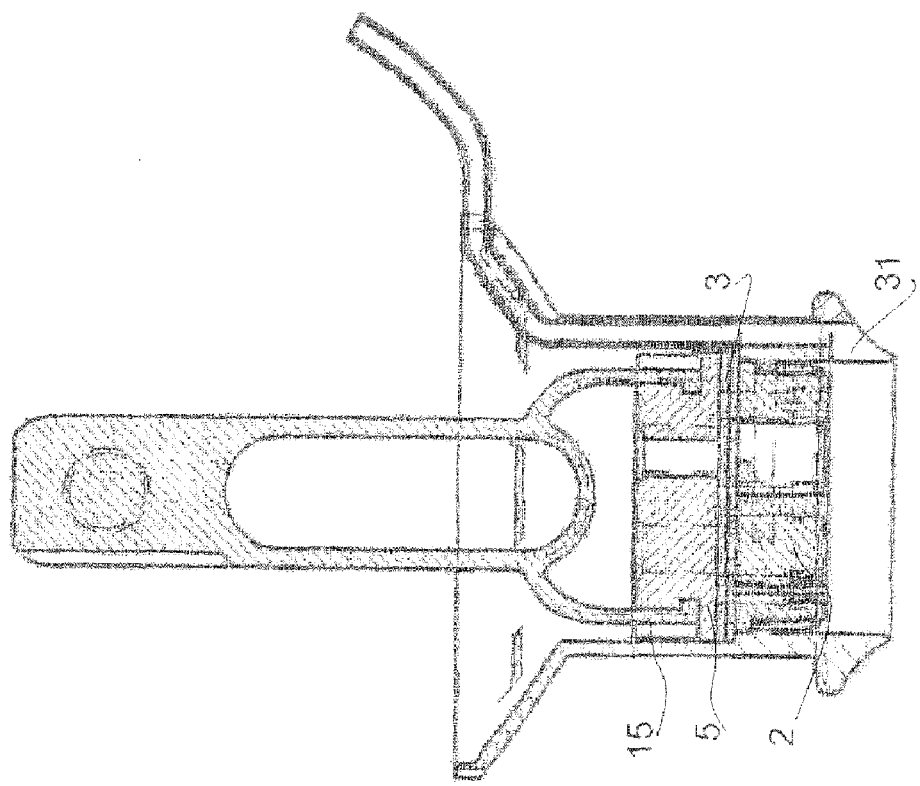

ENDORECTAL TROCAR

CROSS-REFERENCE TO RELATED APPLICATIONS

The present application claims benefit of priority to French Application No. 0758738 filed Oct. 31, 2007.

STATEMENT REGARDING FEDERALLY SPONSORED RESEARCH OR DEVELOPMENT

None.

THE NAMES OF THE PARTIES TO A JOINT RESEARCH AGREEMENT

None.

INCORPORATION-BY-REFERENCE OF MATERIAL SUBMITTED ON A COMPACT DISC

None.

BACKGROUND OF THE INVENTION (1) Field of the Invention

The present invention relates to an endorectal trocar. Specifically, it relates to the field of endoscopy and surgery for intervention by the rectal route, for exploratory or therapeutic procedures. In this context, the term trocar is intended in the broad sense as an accessory suitable for introducing various instruments (particularly in endoscopy) through natural cavities, and in the case of the invention, in the rectum through the anus.

(2) Description of Related Art

In this field, very specific devices are generally employed.

A complex ensemble specifically intended for rectoscopy is known from the document FR 2,536,651, which includes a metallic body suitable for being introduced by the rectal route with a plurality of endoscopy instruments, such as a video camera, endorectal inflation system, or the like, arranged within its interior volume. This complex and costly device comprises multiple pieces.

From its design, it is systematically reusable and requires delicate and costly sterilization steps. In addition, a leak-tight seal surrounding the pathway for the instruments is ensured by a sealing ring added to the exterior of the trocar and located behind the channel for introduction through the rectum. This situation offers less clearance for the instruments introduced, and is implemented by a costly assembly means within the body of the instrument and a sealing ring.

There is thus a need to offer an endorectal trocar that provides more effective cooperation between the sealing means inside the channel for introducing the instruments and the body of the trocar device. There is also a need to improve the steps for the placement of the trocar, notably with regard to the phase for introduction through the anus and the general steps for utilizing the trocar, in particular for implementing its fixation, insufflation with an inflation fluid, etc.

BRIEF SUMMARY OF THE INVENTION

The present invention is of this type and thus offers an improved endorectal trocar. According to this invention, an advantageously single-use trocar comprises an exterior body that defines an internal channel for permitting the passage of instruments or additionally a dilation means that preliminarily facilitates introduction. At the interior surface of the body, a fixing means is envisioned in the middle of the internal channel to work together with a leak-tight barrier that can be added to the interior of the body, or advantageously with dilation means.

The positioning of the leak-tight barrier at the middle of the internal channel facilitates taking full advantage of the large capacity for clearance of the instruments and ensures a larger space for working by the practitioner at the exterior end of the trocar. The fixing means utilized according to the present invention is provided for this purpose within the internal channel and advantageously comprises a rapid fixing means of a type that permits the practitioner initially to arrange for the body to work together with a dilation means for the introduction as well as the withdrawal of said means to replace it with the leak-tight barrier to ensure a leak-tight passageway for the endoscopy instruments.

Being at the middle of the internal channel of the body, the barrier can exhibit an approximately equivalent diameter and can facilitate passage between the passageway and the internal channel without blockage, constriction or misalignment.

All of these operations are carried out very readily due to the design of the trocar, in particular in the preferable case where an implement in the form of a handle is used for positioning the leak-tight barrier.

The design used, and notably that of the leak-tight barrier, moreover ensures having both a less costly design and a highly efficient leak-tight seal such that the assembly not only represents a technical advance but also a cost advantage by avoiding the use of multiple components and their associated sterilization.

Other aims and advantages will become apparent over the course of the description that follows, which presents a preferred embodiment of the invention while not being limiting.

The present invention relates to an endorectal trocar provided with a body for endorectal introduction that defines an open internal channel, a leak-tight barrier that extends across the internal channel and exhibits passageways for rectoscopy instruments, wherein the body and the leak-tight barrier are two distinct assemblies that can be attached by a fixing means at the internal channel.

According to the variants given below, which are not limiting but are preferred, the trocar is such that:

it comprises means for manipulating the leak-tight barrier from the exterior of the internal channel;

the manipulation means comprises handles where the distal end cooperates together in an adjustable manner with the leak-tight barrier;

the distal end of the handle comprises at least two arms that can be applied to a carrier face of the leak-tight barrier;

the arms are elastically deformable between a position of being applied to the carrier face and a free position;

the handle comprises a sleeve with an elastically deformable zone configured to produce the elastic deformation of the arms;

the elastically deformable zone comprises a recess oriented along the longitudinal direction of the handle and formed so as to define a deformable border linked to the arms;

the fixation means comprises a male/female system of locking by rotation;

the device comprises a dilation means that exhibits a distal end that becomes progressively wider and suitable for working together with an internal channel in the absence of a leak-tight barrier;

the exterior surface of the dilation means meets with the distal boundary of body;

the distal end of the dilation means exhibits a rounded exterior surface;

the body and the dilation means can be attached by a fixing means at the internal channel;

the leak-tight barrier comprises a sealing part that is interposed between two attached sides;

the device comprises a longitudinal channelway within the surface layer of the body that receives an inlet tube for an inflation fluid;

the opening of the channelway to the distal end of the trocar has a transverse component; and, the leak-tight barrier is positioned approximately at the midpoint of the length of internal channel.

BRIEF DESCRIPTION OF THE SEVERAL VIEWS OF THE DRAWINGS

The attached figures are provided by way of example and do not limit the invention in any way. They represent only one embodiment of the invention and facilitate the easy understanding thereof.

FIGS. 1 through 3 represent an embodiment of the body of the trocar, with respectively a side-view, a longitudinal section, and a view from above.

FIGS. 10 and 11 show one component of the leak-tight barrier and FIGS. 12 and 13 show a second component.

FIG. 17 is an enlargement of FIG. 15.

FIG. 18 shows one embodiment of the handle in isolation.

DETAILED DESCRIPTION OF THE INVENTION

Figures 4, 5:
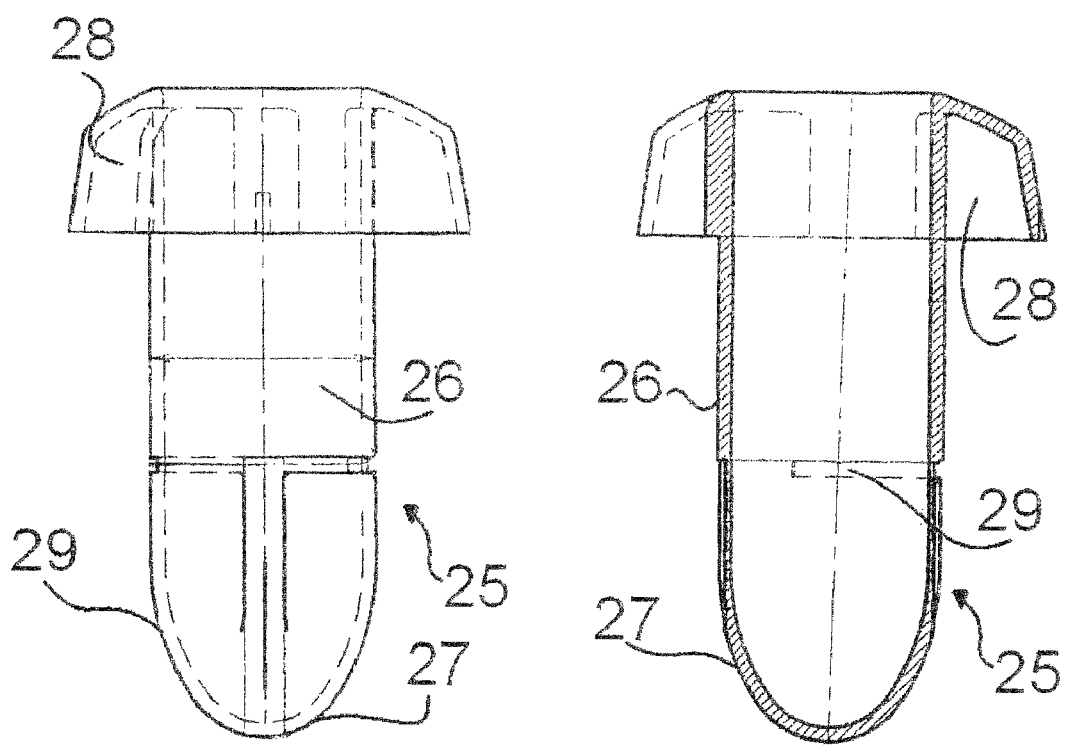
FIGS. 4 through 6 present an embodiment of the dilation means, with respectively a side-view, a longitudinal section, and a view from above.
Figure 6:
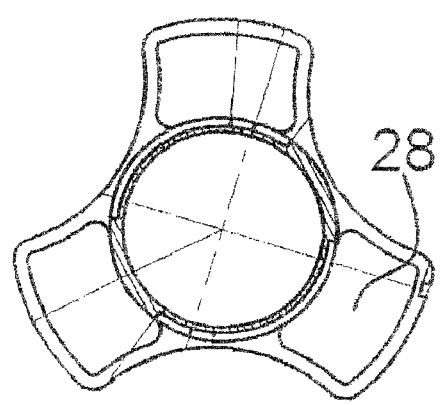

The trocar described, advantageously intended for endoscopy, is preferably designed so as to be disposal after a single use. Thus, the materials utilized are expected to reflect this fact. Notably, except for sealing part 3 that will be described later, the majority of the components are formed from a moulded rigid plastic material. Sealing part 3 can be formed of an elastomeric polymer or silicone.

In addition, the rest of the description follows the convention that the "distal" end of a trocar component is understood to be located toward the interior of the rectum, and thereby is in the lead in the anal introduction. By contrast, the "proximal" end is understood to remain accessible by the practitioner once the trocar has been placed in position.

Body 1 illustrated in FIGS. 1 through 3 comprises an exterior surface that permits the introduction by the rectal route through the intermediary of a first end referred to here as distal boundary 22, the exterior surface of which becomes wider so as to facilitate the introduction and advantageously presents a rim that is raised relative to the rest of body 1 so as to increase the retention of the trocar at the upper edge of the anal canal. Proximal boundary 23 of body 1 remains accessible by the practitioner, notably to carry out the introduction of endoscopy instruments. This end is advantageously flared out so as to offer more working space for the operator, which makes possible freedom of movement near the inlet for the insufflation tube for the inflation fluid, so as to avoid any interference with the movements of the practitioner.

Between the two boundaries 22, 23, body 1 comprises an intermediate portion where the exterior surface is preferentially cylindrical the same as the internal surface that defines internal channel 21 that assures the passage of various instruments that are endoscopy instruments or dilation means 25. Internal channel 21 advantageously has a cylindrical cross-section that continues for along the length of the trocar without any restriction that would hinder the simultaneous passage of a plurality of instruments. A plurality of lumens 24 formed on the flared out part of proximal boundary 23 permit an attachment between the trocar and the body of the patient by sutures.

The internal surface of body 1 additionally comprises fixation means 6, the function of which will be clarified later in the specification and can comprise two diametrically opposed protuberances visible in FIGS. 2 and 3 that constitute the male bodies that work together with the corresponding inner surfaces on the other components for attachment to body 1.

Fixation means 6 is generally located at the interior of internal channel 21 approximately at the half-way point of its length for positioning the leak-tight barrier at this point. Generally, the leak-tight barrier and the fixation means are advantageously located in the central third of the length of the internal channel.

Body 1 moreover advantageously comprises channelway 19 oriented along the longitudinal direction and extending from the proximal part to the distal part of body 1 so as to receive tube 20 visible in FIGS. 8, 9, 15 and 16 for providing the inflation fluid. This implementation simplifies the design of the manufacturing of body 1, in particular by injection moulding.

Channelway 19 is, for example, a groove moulded in body 1 or machined, within which is mounted tube 20 that can also be fitted in, namely by simple embedding within the groove. At its distal part, channelway 19 comprises an opening, shown more precisely in FIG. 17 by the number 31, so as to facilitate the discharge of the inflation gas into the human body.

In the case depicted, opening 31 comprises an exit for the fluid that is both longitudinal and transverse. The transverse component is advantageously to avoid the inopportune obstruction of the inflation circuit, which in particular can be produced by the mucosa. In the case depicted, a portion of the inflation gas is oriented toward the distal opening of internal channel 21.

Figure 7:
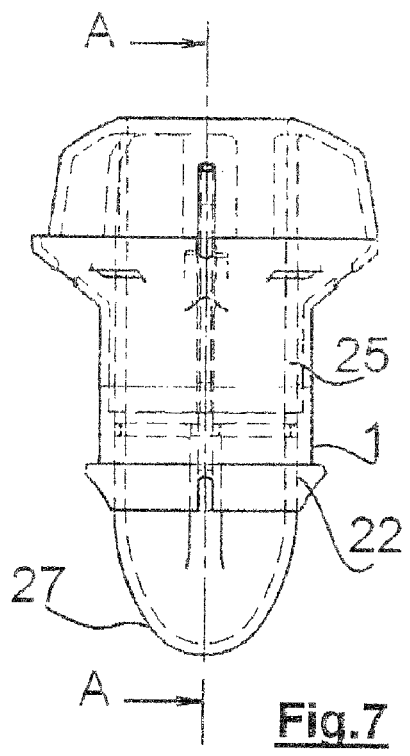
FIGS. 7 through 9 similarly portray how the body and the dilation means work together.
Figure 8:
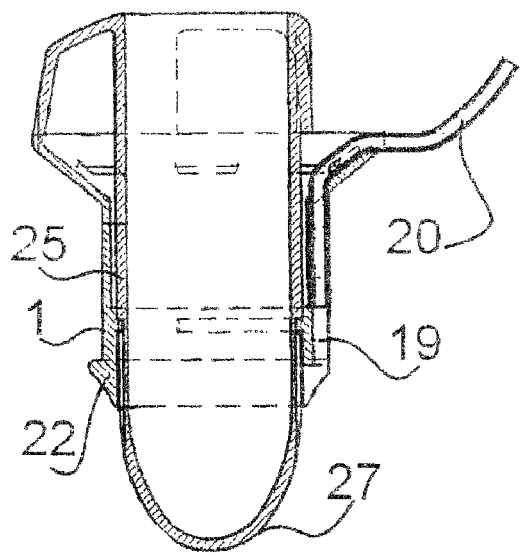
Figure 9:
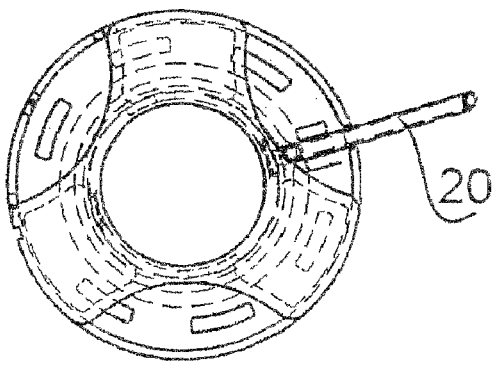
Figures 14, 15:
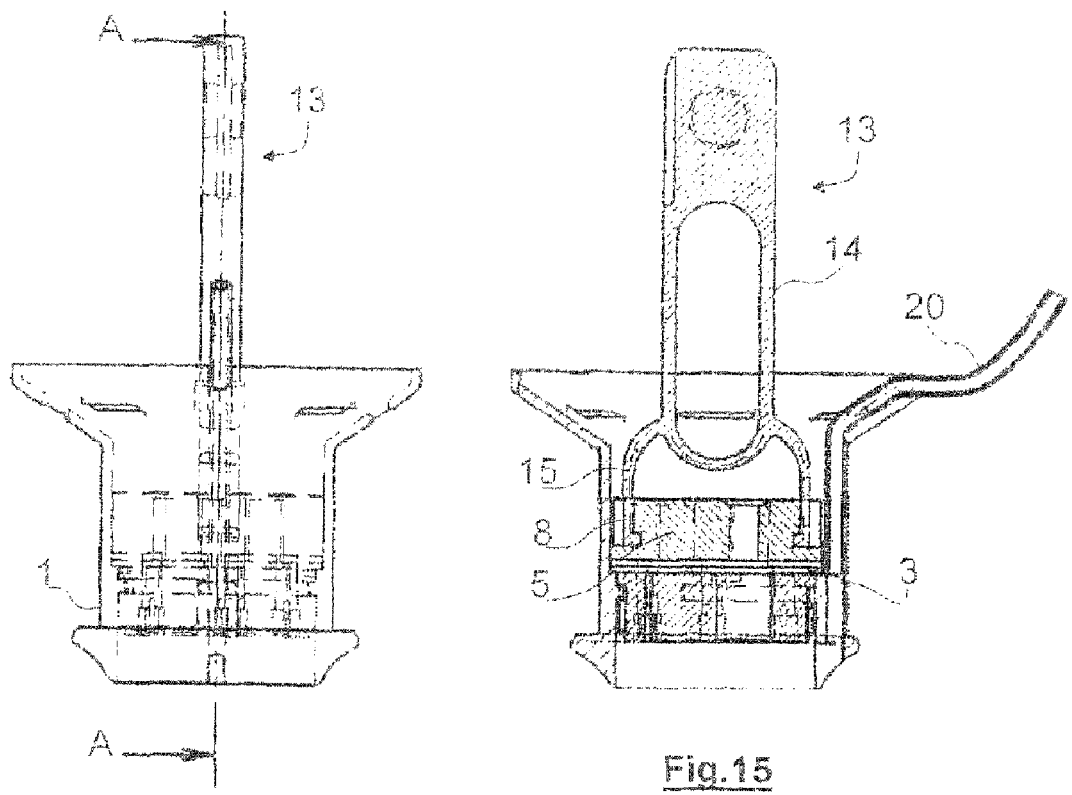
FIGS. 14 through 16 illustrate how the body and the leak-tight barrier work together, with respectively a side-view, a longitudinal section, and a view from above.
Figure 16:
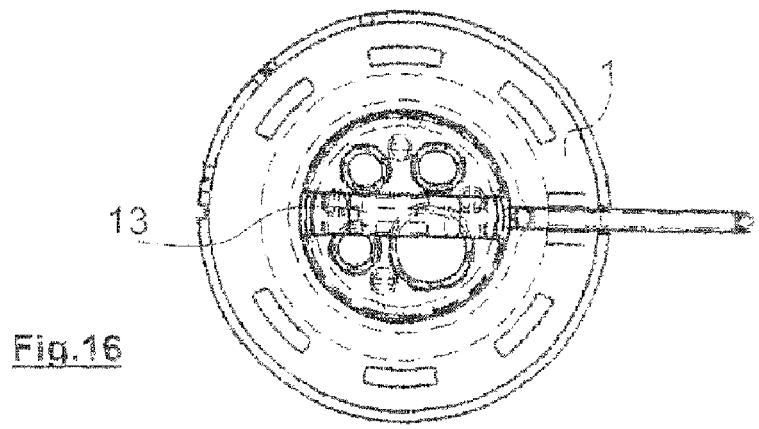

The potential contributions by the trocar with respect to ergonomics for the practitioner and for the introduction of instruments are greater with a larger diameter of body 1. In order to use a trocar that is large enough, body 1 works together advantageously according to the present invention with dilation means 25 that comprises longitudinal zone 26 substantially elongated and which can be introduced through internal channel 21 of body 1. Dilation means 25 moreover comprises distal end 27 having a progressive circular cross-section and gripping zone 28 located opposite to distal end 27 so as to facilitate the manipulations of the practitioner. Component 28 is advantageously applied to the circumference of boundary 23 of body 1 as is seen in FIGS. 7 through 9.

Indentation 29 is formed on the exterior surface of longitudinal zone 26 of dilation means 25 so as to correspond to fixation means 6 of the internal surface of body 1 and to permit them to work together. In particular, the longitudinal translation of dilation means 25 within internal channel 21 is followed by a rotation over an angle that is limited so as to pass by fixation means 6 working together with a longitudinal portion of indentation 29 at a radial portion of this indentation.

Once positioned and assembled, dilation means 25 ensures that introduction through the patient's natural cavity is facilitated. The comfort is also much greater when distal end 27 of dilation means 25 has a form that is aligned with the continuity of the exterior surface of distal boundary 22 of body 1. This continuity is particularly visible in FIGS. 7 and 8. It is readily understood that the introduction is perfectly gradual on the rounded portion of the distal end of dilation means 25 until it reaches boundary 22 and its retention rim suitable for fixing the position of body 1 relative to the natural cavity.

FIGS. 10 through 13 depict another view of the trocar with the specific design of leak-tight barrier 2. This barrier 2 has the function of ensuring the peripheral leak-tight seal with body 1 and the leak-tight seal at each of the passageways 9, 10, 11 and 12 that allow the introduction of endoscopy instruments. The number of passageways 9, 10, 11 and 12 is not limited regarding either their diameter or their configuration. By way of example, shown [here] is the formation of three passageways 10, 11 and 12 that have a first diameter and the implementation of passageway 9 with a much larger diameter that can adapt to various types of instrument.

In the case shown, leak-tight barrier 2 is formed in a plurality of components, namely distal side 4 that works together with proximal side 5 so as to frame sealing part 3 held in a clamp. The assembly means between the two sides 4, 5 are not limited, and depicted [here] is a representative preferred embodiment of a plurality of linking pins 30 that jut out from the interior surface of proximal side 5 and can be introduced into joint collars 7 formed to correspond through distal side 4. An indented end with a conical portion equipped with a rim at pins 30 ensure a locking when the introduction of pins 30 into joint collars 7 is complete. This assembly is performed after sealing part 3 made of a flexible material such as an elastomer is positioned in an intercalary fashion. The ensemble of sides 4, 5 and sealing part 3 is obviously formed so as to present the collars corresponding to the constitution of each of passageways 9, 10, 11 and 12. Sealing part 3 advantageously has a diameter that is slightly larger for being applied to the interior surface of body 1. Likewise, its diameter at each passageway 9, 10, 11 and 12 is advantageously slightly smaller so as to constitute a sealing contact surrounding the instruments to be introduced.

It is readily understood that this design for leak-tight barrier 2 ensures both the efficient maintenance in position of sealing part 3 that can be selected according to sealing capability considerations as well as that the rigidification and mechanical resistance of the barrier are due to sides 4 and 5. A perfectly leak-tight seal is thus obtained without much of an impact on the mechanical resistance of the leak-tight barrier.

In a manner similar to the working together between body 1 and dilation means 25, leak-tight barrier 2 is arranged so as to be susceptible to working together with fixing means 6. Thus, indentation 29 arranged with a longitudinal portion and a radial portion is constituted on the distal side 4 for the introduction of fixation means 6 and locking by rotation.

Of course, this configuration is only representative and not limiting.

Due to the presence of leak-tight barrier 2 amid channel 21, it is preferable to implement its placement in position through the use of an ad hoc implement that can be constituted by handle 13 that appears in detail in FIG. 18, where FIGS. 14 through 17 illustrate how it works together with leak-tight barrier 2.

This handle 13 constitutes an activation means that is distant from leak-tight barrier 2 that permits the manipulation to the proximal end of the trocar for transport. The alternatives to handle 13 explained below are within the scope of the present invention. In particular, leak-tight barrier 2 can be connected to a hollow cylindrical sleeve of small thickness and applied to the internal surface of body 1 between leak-tight barrier 2 and proximal boundary 23 so as to constitute an activation means for transporting the leak-tight barrier.

In the case illustrated, handle 13 comprises sleeve 14, a portion of which possesses recess 17 here in the form of an oblong pin oriented along the longitudinal axis of handle 13 and that permits the definition of elastically deformable boundary 18, in particular by compression between two fingers of the practitioner. Boundary 18 itself is linked with arms 15 that number two in the case illustrated. The distal end of arms 15 comprise rim 16 suitable for working together with a corresponding portion within crenellations 8 formed in proximal side 5 of leak-tight barrier 2. Crenellations 8 form a carrier face for the mobility of leak-tight barrier 2 that function to work together with handle 13.

Advantageously, arms 15 are elastically deformable so as to travel past a locking position relative to crenellations 8 at a free position for being placed in position or being withdrawn. To this end, an elastic deformation of boundary 18 is beneficial for inducing separation or connection of arms 15. More precisely, the practitioner pressing on the parallel longitudinal edges of boundary 18 induces their connection and deformation of the intermediate portion of boundary 18 induces a rotation of arms 15 that tends to separate them. On the other hand, a relaxation of the pressure by the practitioner permits the ensemble to return to its resting position.

The placement in position of leak-tight barrier 2 within body 1 is thus performed in a transporting manner that is particularly easy for the practitioner. Indeed, once leak-tight barrier 2 is attached to handle 13, the practitioner needs only to perform the introduction within the internal channel 21 without any interference with the internal surface of body 1. Once the placement in position is performed, it is sufficient to rotate leak-tight barrier 2 over a limited angle (for example, on the order of 30°) to fix it relative to body 1.

The introduction of the endoscopy instruments can then be performed.

Notably, leak-tight barrier 2 constitutes an added, adjustable component that can easily be replaced in case of problems with the leak-tight seal or if its configuration (number of pins, diameter) is no longer appropriate for the exploratory or surgical manipulations that the practitioner desires to perform. That being the case, one can also envision a definitive attachment guaranteed against incidents during the operational phase.

REFERENCES

1. Body
2. Leak-tight barrier
3. Sealing part
4. Distal side
5. Proximal side
6. Fixing means
7. Joint collars
8. Crenellation
9. Passageway
10. Passageway
11. Passageway
12. Passageway
13. Handle
14. Sleeve
15. Arm
16. Rim
17. Recess 18. Deformable boundary
19. Channelway
20. Tube
21. Internal channel
22. Distal boundary
23. Proximal boundary
24. Suture lumen
25. Dilation means
26. Longitudinal zone
27. Distal end
28. Gripping zone
29. Indentation
30. Linking pin
31. Opening

The invention claimed is:

1. An endorectal trocar provided with:
   a—a body (1) for endorectal introduction that defines an open internal channel (21), and
   b—a leak-tight barrier (2) that extends across the internal channel (21) and exhibits passageways (9, 10, 11, 12) for engaging rectoscopy instruments,
   wherein the body (1) and the leak-tight barrier (2) are two distinct assemblies that can be attached by fixing means (6) at the internal channel (21),
   wherein the leak-tight barrier is arranged substantially at mid length of the internal channel according to a mobile assembly,
   wherein the leak-tight barrier comprises a driving surface (8) configured to accept a handling means of the leak-tight barrier (2) from outside the internal channel (21), said handling means being configured in the form a handle (13) with arms (15) to cooperate with the driving surface (8) of the leak-tight barrier, and
   wherein the positioning or removal of the leak-tight barrier is performed by an additional rotation operation of the leak-tight barrier with respect to the body (1).

2. The trocar according to claim 1, wherein the handling means comprises a handle (13) having a distal end that cooperates together in an adjustable manner with the leak-tight barrier (2).

3. The trocar according to claim 2, wherein the distal end of the handle (13) comprises at least two arms (15) that can be applied to a carrier face of the leak-tight barrier (2).

4. The trocar according to claim 3, wherein the arms (15) are elastically deformable between a position of being applied to the carrier face and a free position.

5. The trocar according to claim 4, wherein the handle (13) comprises a sleeve (14) with an elastically deformable zone configured to produce the elastic deformation of the arms (15).

6. The trocar according to claim 5, wherein the elastically deformable zone comprises a recess (17) oriented along the longitudinal direction of the handle (13) and formed so as to define a deformable border (18) linked to the arms (15).

7. The trocar according to claim 1, that comprises a dilation means (25) with a distal end becoming progressively wider and suitable for working together with the internal channel (21) in the absence of the leak-tight barrier (2).

8. The trocar according to claim 7, wherein an exterior surface of the dilation means (25) meets with a distal boundary (22) of the body (1).

9. The trocar according to claim 8, wherein the distal end of the dilation means exhibits a rounded exterior surface.

10. The trocar according to claim 8, wherein the body (1) and the dilation means (25) can be attached by the fixing means at the internal channel (21).

11. The trocar according to claim 7, wherein the distal end of the dilation means exhibits a rounded exterior surface.

12. The trocar according to claim 11, wherein the body (1) and the dilation means (25) can be attached by the fixing means at the internal channel (21).

13. The trocar according to claim 7, wherein the body (1) and the dilation means (25) can be attached by the fixing means at the internal channel (21).

14. The trocar according to claim 1, further comprising a longitudinal channelway (19) in the wall of the body (1) that receives an inlet tube (20) for an inflation fluid.

15. The trocar according to claim 14, wherein an opening of the channelway (19) to the distal end of the trocar has a transverse component.

16. The trocar according to claim 1, wherein the leak-tight barrier (2) comprises a distal side (4) cooperating with a proximal side (5) between which a sealing part (3) is arranged and taken up and wherein the leak-tight barrier (2) is provided with drive surfaces to cooperate with the handle (1), the means being slots formed on the proximal side (5) of the barrier.

* * * * *